US012788250B2

(12) United States Patent
Sugiyama et al.

(10) Patent No.: US 12,788,250 B2
(45) Date of Patent: Nov. 10, 2026

(54) DETECTION DEVICE

(71) Applicant: Magnolia White Corporation, Tokyo (JP)

(72) Inventors: Hiroki Sugiyama, Tokyo (JP); Takahiro Shoji, Tokyo (JP); Yoshihide Ohue, Tokyo (JP); Kaoru Taketa, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 365 days.

(21) Appl. No.: 18/387,992

(22) Filed: Nov. 8, 2023

(65) Prior Publication Data

US 2024/0148251 A1 May 9, 2024

(30) Foreign Application Priority Data

Nov. 9, 2022 (JP) ................................ 2022-179623

(51) Int. Cl.
*A61B 5/00* (2006.01)

(52) U.S. Cl.
CPC .................................. *A61B 5/0059* (2013.01)

(58) Field of Classification Search
CPC .............. A61B 5/0059; A61B 5/02427; A61B 5/14552; A61B 5/489; A61B 2562/12;
(Continued)

(56) References Cited

U.S. PATENT DOCUMENTS 4,855,802 A * 8/1989 Kato .................... H10F 39/191 257/443
2008/0237758 A1 10/2008 Okada
(Continued)

FOREIGN PATENT DOCUMENTS

CA 2127297 * 11/2003
JP 2008-244411 A 10/2008
(Continued)

OTHER PUBLICATIONS

Machine Translation of WO-2017150295-A1, Patent Translate, pp. 1-8, printed of Jan. 25, 2026, (Year: 2017).*
(Continued)

*Primary Examiner* — Jennifer Robertson
*Assistant Examiner* — Om Patel
(74) *Attorney, Agent, or Firm* — K&L Gates LLP

(57) ABSTRACT

According to an aspect, a detection device includes: a substrate; a photodiode in which a lower electrode, a semiconductor layer, and an upper electrode are stacked on the substrate in the order as listed; a transistor provided in the photodiode; an insulating layer provided between layers of the substrate and the photodiode; and a planarizing layer covering the insulating layer. The insulating layer comprises a projecting portion that projects toward the photodiode in a direction orthogonal to the substrate. The planarizing layer has a contact hole provided in a position that is below the photodiode and overlaps the projecting portion of the insulating layer. The photodiode is provided on an upper side of the planarizing layer and is also provided so as to cover the contact hole. The lower electrode of the photodiode is electrically coupled to the transistor at a bottom of the contact hole.

8 Claims, 10 Drawing Sheets

(58) Field of Classification Search

CPC . A61B 2562/246; H10F 39/016; H10F 39/12; H10F 39/811; H10F 99/00; H10F 39/802; H10F 39/803; H10F 39/18; H01L 25/167; H01L 23/5384; G01J 1/44; G01J 1/46; G01J 2001/448; G01J 2001/446

See application file for complete search history.

(56) References Cited

U.S. PATENT DOCUMENTS

| | | | |
|---|---|---|---|
| 2009/0026509 | A1 | 1/2009 | Hayashi et al. |
| 2012/0038018 | A1 | 2/2012 | Yamada et al. |
| 2013/0149809 | A1 | 6/2013 | Yamada et al. |
| 2015/0021613 | A1 | 1/2015 | Hayashi et al. |
| 2023/0379599 | A1 | 11/2023 | Saito et al. |

FOREIGN PATENT DOCUMENTS

| | | | | | |
|---|---|---|---|---|---|
| JP | 2008283113 | A | | 11/2008 | |
| JP | 2012039004 | A | | 2/2012 | |
| JP | 2022-121297 | A | | 8/2022 | |
| WO | WO-2016195000 | A1 | * | 12/2016 | ............. H10D 30/67 |
| WO | WO-2017150295 | A1 | * | 9/2017 | ............. H04N 25/70 |

OTHER PUBLICATIONS

Machine Translation of WO-2016195000-A1, Patent Translate, pp. 1-21, printed of Jan. 25, 2026, (Year: 2016).*

Office Action mailed on May 12, 2026 in corresponding Japanese Patent Application No. 2022-179623 and English translation of same. 9 pages.

* cited by examiner

DETECTION DEVICE

CROSS-REFERENCE TO RELATED APPLICATION

This application claims the benefit of priority from Japanese Patent Application No. 2022-179623 filed on Nov. 9, 2022, the entire contents of which are incorporated herein by reference.

BACKGROUND

1. Technical Field

What is disclosed herein relates to a detection device.

2. Description of the Related Art

Japanese Patent Application Laid-open Publication No. 2008-283113 (JP-A-2008-283113) and Japanese Patent Application Laid-open Publication No. 2012-039004 (JP-A-2012-039004) each describes a detection device (described as a photosensor and a photoelectric conversion element in JP-A-2008-283113 and JP-A-2012-039004, respectively) in which a plurality of positive-intrinsic-negative (PIN) photodiodes are arranged on a substrate. The PIN photodiodes are mounted on what is called an active matrix array substrate on which a plurality of transistors are arranged in a matrix having a row-column configuration.

Such a detection device is provided with contact holes for electrically coupling the transistors to the photodiodes. In JP-A-2008-283113, the photodiodes are provided in areas that do not overlap steps formed by the contact holes. In JP-A-2012-039004, p-type semiconductor layers of the photodiodes are provided in the areas that do not overlap the steps formed by the contact holes.

The steps formed by the contact holes or the like may cause leak paths between lower electrodes and upper electrodes of the photodiodes. In JP-A-2008-283113 and JP-A-2012-039004, the arrangement of the photodiodes is restricted by the positional relation between the transistors and the contact holes. This restriction may reduce the effective light-receiving area of the photodiodes, resulting in a reduction in detection sensitivity.

SUMMARY

According to an aspect, a detection device includes: a substrate; a photodiode in which a lower electrode, a semiconductor layer, and an upper electrode are stacked on the substrate in the order as listed; a transistor provided in the photodiode; an insulating layer provided between layers of the substrate and the photodiode; and a planarizing layer covering the insulating layer. The insulating layer comprises a projecting portion that projects toward the photodiode in a direction orthogonal to the substrate. The planarizing layer has a contact hole provided in a position that is below the photodiode and overlaps the projecting portion of the insulating layer. The photodiode is provided on an upper side of the planarizing layer and is also provided so as to cover the contact hole. The lower electrode of the photodiode is electrically coupled to the transistor at a bottom of the contact hole.

DETAILED DESCRIPTION

Figure 1:
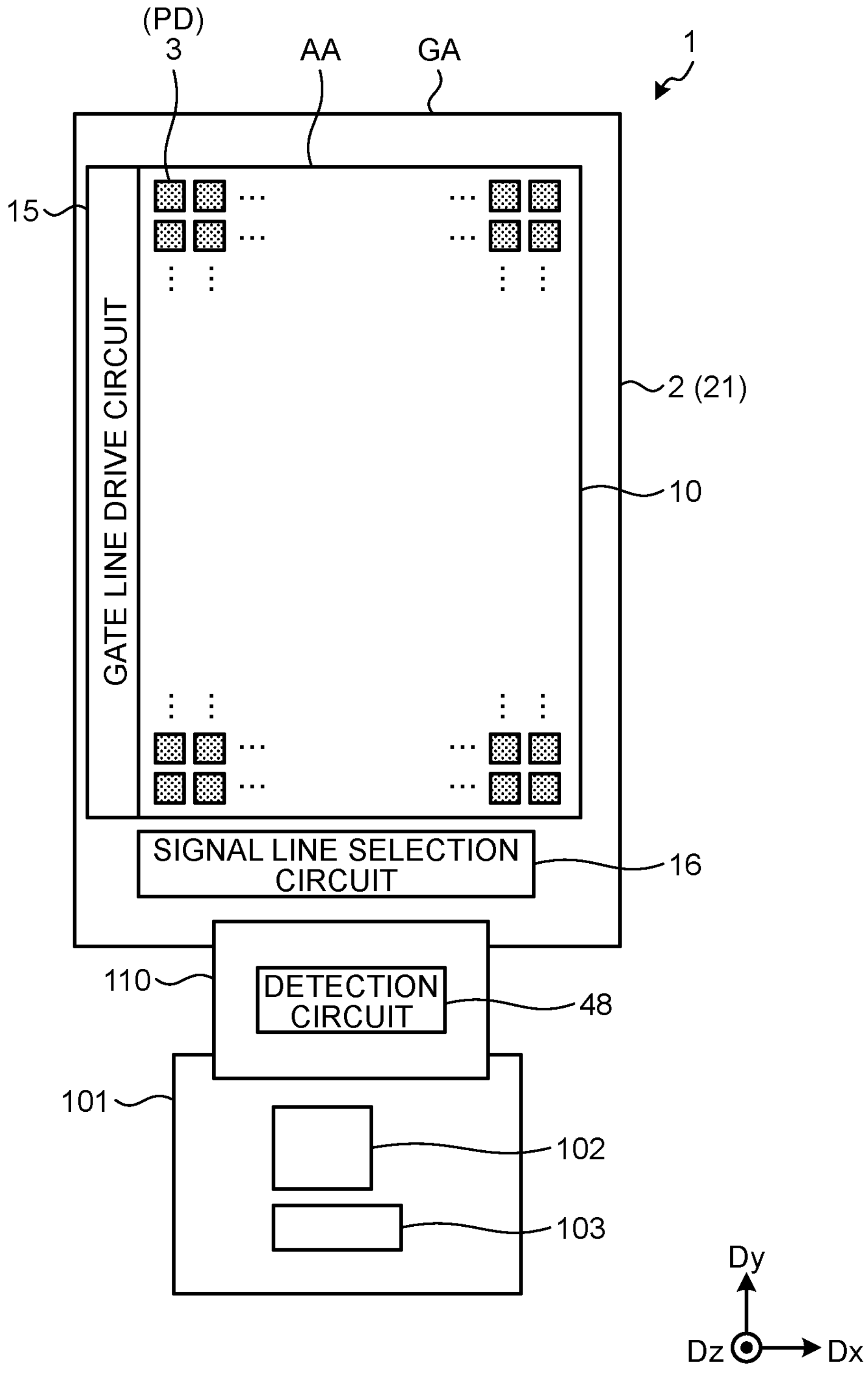
FIG. 1 is a plan view schematically illustrating a detection device according to a first embodiment.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the present disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present disclosure and the drawings, and detailed description thereof may not be repeated where appropriate.

In the present specification and claims, in expressing an aspect of disposing another structure on or above a certain structure, a case of simply expressing “on” includes both a case of disposing the other structure immediately on the certain structure so as to contact the certain structure and a case of disposing the other structure above the certain structure with still another structure interposed therebetween, unless otherwise specified.

First Embodiment

FIG. 1 is a plan view schematically illustrating a detection device according to a first embodiment. As illustrated in FIG. 1, a detection device 1 includes an array substrate 2 (substrate 21), a sensor 10, a gate line drive circuit 15, a signal line selection circuit 16, a detection circuit 48, a control circuit 102, and a power supply circuit 103.

The substrate 21 is electrically coupled to a control substrate 101 through a wiring substrate 110. The wiring substrate 110 is, for example, a flexible printed circuit board or a rigid circuit board. The wiring substrate 110 is provided with the detection circuit 48. The control substrate 101 is provided with the control circuit 102 and the power supply circuit 103. The control circuit 102 is, for example, a field-programmable gate array (FPGA). The control circuit

102 supplies control signals to the sensor 10, the gate line drive circuit 15, and the signal line selection circuit 16 to control a detection operation of the sensor 10. The power supply circuit 103 supplies voltage signals including, for example, a power supply potential SVS (refer to FIG. 3) to the sensor 10 and the gate line drive circuit 15.

The substrate 21 has a detection area AA and a peripheral area GA. The detection area AA is an area provided with a plurality of photodiodes PD. The peripheral area GA is an area between the outer perimeter of the detection area AA and the edges of the substrate 21, and is an area not provided with the photodiodes PD. The gate line drive circuit 15 and the signal line selection circuit 16 are provided in the peripheral area GA of the substrate 21.

In the following description, a first direction Dx is one direction in a plane parallel to the substrate 21. A second direction Dy is one direction in the plane parallel to the substrate 21 and is a direction orthogonal to the first direction Dx. The second direction Dy may non-orthogonally intersect the first direction Dx. A third direction Dz is a direction orthogonal to the first direction Dx and the second direction Dy. The third direction Dz is a direction normal to the substrate 21. The term "plan view" refers to a positional relation when viewed from a direction orthogonal to the substrate 21.

A plurality of sensor pixels 3 (photodiodes PD) are arranged in a matrix having a row-column configuration in the detection area AA. In other words, the sensor pixels 3 (photodiodes PD) are arranged in the first direction Dx and the second direction Dy in the detection area AA. Herein, each of the sensor pixels 3 of the sensor 10 is an optical sensor that includes, as a sensor element, a corresponding one of the photodiodes PD, a capacitive element Ca, and a transistor Tr (refer to FIG. 3).

Each of the photodiodes PD outputs an electrical signal corresponding to light emitted thereto. More specifically, the photodiode PD is a positive-intrinsic-negative (PIN) photodiode. Each of the photodiodes PD included in the sensor pixels 3 performs detection in accordance with a gate drive signal VGL supplied from the gate line drive circuit 15. Each of the photodiodes PD outputs the electrical signal corresponding to the light emitted thereto as a detection signal Vdet to the signal line selection circuit 16. The detection device 1 detects information on a living body based on the detection signals Vdet received from the photodiodes PD.

Figure 2:
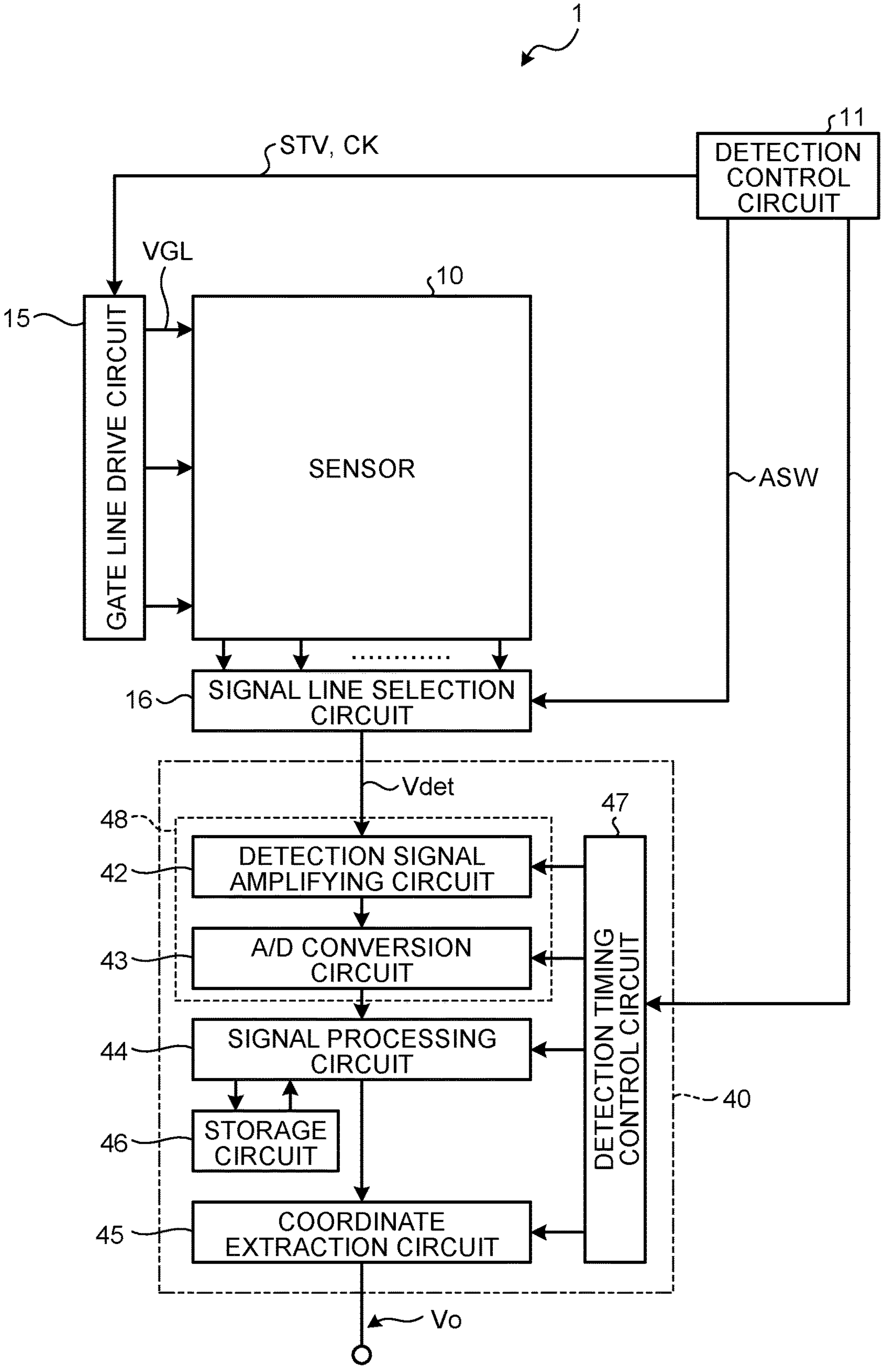
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection control circuit 11 and a detector 40. The control circuit 102 includes one, some, or all functions of the detection control circuit 11. The control circuit 102 also includes one, some, or all functions of the detector 40 other than those of the detection circuit 48.

The detection control circuit 11 is a circuit that supplies respective control signals to the gate line drive circuit 15, the signal line selection circuit 16, and the detector 40 to control operations thereof. The detection control circuit 11 supplies various control signals including, for example, a start signal STV and a clock signal CK to the gate line drive circuit 15. The detection control circuit 11 also supplies various control signals including, for example, a selection signal ASW to the signal line selection circuit 16.

The gate line drive circuit 15 is a circuit that drives a plurality of gate lines GL (refer to FIG. 4) based on the various control signals. The gate line drive circuit 15 sequentially or simultaneously selects the gate lines GL, and supplies the gate drive signals VGL to the selected gate lines GL. Through this operation, the gate line drive circuit 15 selects the photodiodes PD coupled to the gate lines GL.

Figure 4:
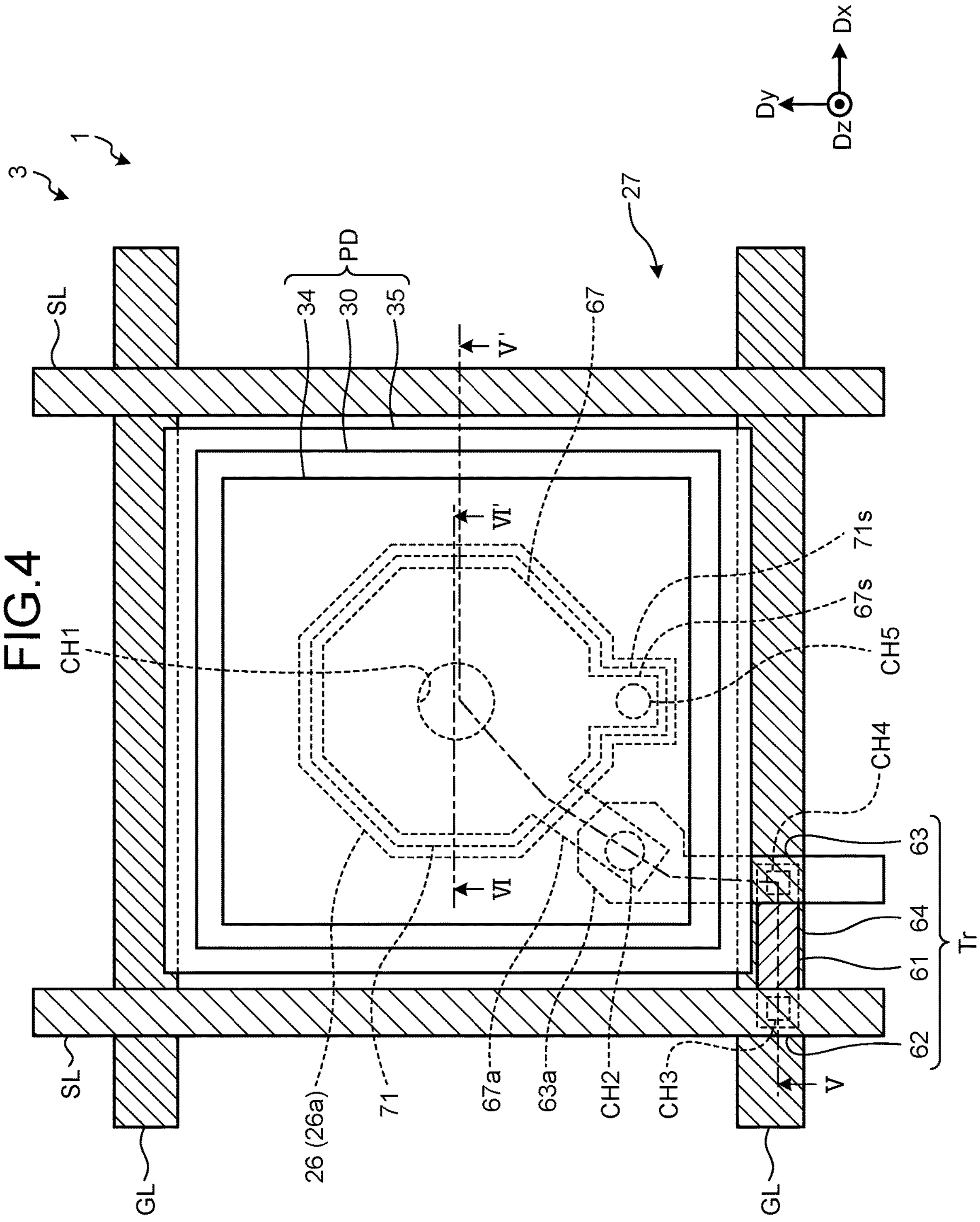
FIG. 4 is a plan view schematically illustrating a photodiode and a transistor according to the first embodiment.

The signal line selection circuit 16 is a switch circuit that sequentially or simultaneously selects a plurality of signal lines SL (refer to FIG. 4). The signal line selection circuit 16 is, for example, a multiplexer. The signal line selection circuit 16 couples the selected signal lines SL to the detection circuit 48 based on the selection signal ASW supplied from the detection control circuit 11. Through this operation, the signal line selection circuit 16 outputs the detection signals Vdet of the photodiodes PD to the detector 40.

The detector 40 includes the detection circuit 48, a signal processing circuit 44, a coordinate extraction circuit 45, a storage circuit 46, and a detection timing control circuit 47. The detection timing control circuit 47 performs control to cause the detection circuit 48, the signal processing circuit 44, and the coordinate extraction circuit 45 to operate in synchronization with one another based on a control signal supplied from the detection control circuit 11.

The detection circuit 48 is, for example, an analog front-end (AFE) circuit. The detection circuit 48 is a signal processing circuit having functions of at least a detection signal amplifying circuit 42 and an analog-to-digital (A/D) conversion circuit 43. The detection signal amplifying circuit 42 is a circuit that amplifies the detection signals Vdet, and is an integration circuit, for example. The A/D conversion circuit 43 converts analog signals output from the detection signal amplifying circuit 42 into digital signals.

The signal processing circuit 44 is a logic circuit that detects a predetermined physical quantity received by the sensor 10 based on output signals of the detection circuit 48. The signal processing circuit 44 can detect asperities on a surface of a finger or a palm based on the signals from the detection circuit 48 when an object to be detected such as the finger is in contact with or in proximity to a detection surface. The signal processing circuit 44 may detect the information on the living body based on the signals from the detection circuit 48. Examples of the information on the living body include a vascular image, pulse waves, pulsation, and a blood oxygen saturation level of the finger or the palm.

The storage circuit 46 temporarily stores therein signals calculated by the signal processing circuit 44. The storage circuit 46 may be, for example, a random-access memory (RAM) or a register circuit.

The coordinate extraction circuit 45 is a logic circuit that obtains detected coordinates of the asperities on the surface of the object to be detected such as the finger when the contact or proximity of the object to be detected such as the finger is detected by the signal processing circuit 44. The coordinate extraction circuit 45 is the logic circuit that also obtains detected coordinates of blood vessels in the finger or the palm. The coordinate extraction circuit 45 combines the detection signals Vdet output from the sensor pixels 3 of the sensor 10 to generate two-dimensional information indicating the shape of the asperities on the surface of the object to be detected such as the finger. The coordinate extraction circuit 45 may output the detection signals Vdet as sensor outputs Vo instead of calculating the detected coordinates.

Figure 3:
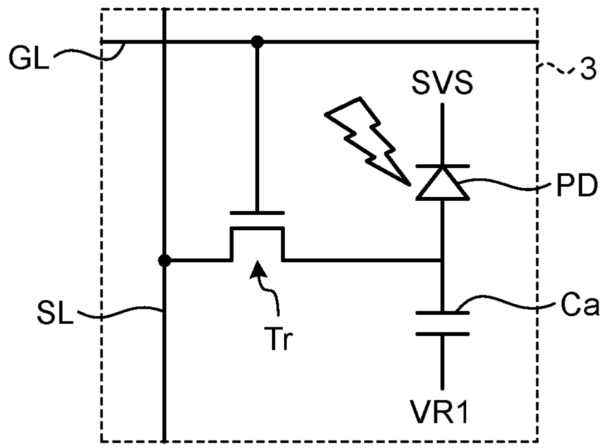
FIG. 3 is a circuit diagram illustrating a sensor pixel of the detection device according to the first embodiment.

The following describes a circuit configuration example and an operation example of the detection device 1. FIG. 3 is a circuit diagram illustrating the sensor pixel of the detection device according to the first embodiment. As illustrated in FIG. 3, the sensor pixel 3 includes the photodiode PD, the capacitive element Ca, and the transistor Tr. The transistor Tr is provided correspondingly to the photodiode PD. The transistor Tr is formed of a thin-film transistor, and in this example, formed of an n-channel metal oxide semiconductor (MOS) thin-film transistor (TFT). The gate of the transistor Tr is coupled to a corresponding one of the gate lines GL. The source of the transistor Tr is coupled to a corresponding one of the signal lines SL. The drain of the transistor Tr is coupled to the anode of the photodiode PD and the capacitive element Ca.

The cathode of the photodiode PD is supplied with the power supply potential SVS from the power supply circuit 103. The capacitive element Ca is supplied with a reference potential VR1 that serves as an initial potential of the capacitive element Ca from the power supply circuit 103.

When the sensor pixel 3 is irradiated with light, a current corresponding to the amount of the light flows through the photodiode PD. As a result, an electric charge is stored in the capacitive element Ca. After the transistor Tr is turned on, a current corresponding to the electric charge stored in the capacitive element Ca flows through the signal line SL. The signal line SL is coupled to the detection circuit 48 through the signal line selection circuit 16. Thus, the detection device 1 can detect a signal corresponding to the amount of the light received by the photodiode PD for each of the sensor pixels 3.

While FIG. 3 illustrates one of the sensor pixels 3, the gate line GL and the signal line SL are each coupled to a plurality of the sensor pixels 3. Specifically, the gate line GL extends in the first direction Dx (refer to FIG. 1), and is coupled to the sensor pixels 3 (transistors Tr) arranged in the first direction Dx. The signal line SL extends in the second direction Dy, and is coupled to the sensor pixels 3 (transistors Tr) arranged in the second direction Dy.

The transistor Tr is not limited to being formed of an n-type TFT and may be formed of a p-type TFT. The sensor pixel 3 may be provided with a plurality of transistors corresponding to one photodiode PD.

The following describes a detailed configuration of the detection device 1. FIG. 4 is a plan view schematically illustrating the photodiode and the transistor according to the first embodiment. As illustrated in FIG. 4, the sensor pixel 3 is an area surrounded by the gate lines GL and the signal lines SL. The gate lines GL each extend in the first direction Dx and are arranged with gaps interposed therebetween in the second direction Dy. The signal lines SL each extend in the second direction Dy and are arranged with gaps interposed therebetween in the first direction Dx.

The photodiode PD is provided in the area surrounded by the gate lines GL and the signal lines SL. The photodiode PD includes an upper electrode 34, a semiconductor layer 30, and a lower electrode 35. The upper electrode 34 and the lower electrode 35 are provided corresponding to each of the photodiodes PD. The lower electrode 35 is, for example, an anode electrode of the photodiode PD. The upper electrode 34 is, for example, a cathode electrode of the photodiode PD.

The outline shape of the upper electrode 34, the semiconductor layer 30, and the lower electrode 35 of the photodiode PD is substantially quadrilateral in plan view. However, the outline shape of the upper electrode 34, the semiconductor layer 30, and the lower electrode 35 is not limited thereto and may be other shapes such as a polygonal shape and a circular shape. Alternatively, the upper electrode 34, the semiconductor layer 30, and the lower electrode 35 may have, for example, an irregular outline shape partially provided with a cutout.

The transistor Tr is provided near an intersection of the gate line GL and the signal line SL. The transistor Tr includes a semiconductor layer 61, a source electrode 62, a drain electrode 63, and a gate electrode 64.

The semiconductor layer 61 is provided so as to extend in the first direction Dx and overlap the gate line GL in plan view. One end side of the semiconductor layer 61 is coupled to the source electrode 62 through a contact hole CH3. The other end side of the semiconductor layer 61 is coupled to the drain electrode 63 through a contact hole CH4.

The semiconductor layer 61 is an oxide semiconductor. The semiconductor layer 61 is more preferably a transparent amorphous oxide semiconductor (TAOS) among oxide semiconductors. Using an oxide semiconductor as the transistor Tr can reduce a leakage current of the transistor Tr. That is, the transistor Tr can reduce the leakage current from the sensor pixel 3 that is not selected. As a result, the detection device 1 can improve the signal-to-noise ratio (S/N). The semiconductor layer 61 is, however, not limited to this material and may be formed of, for example, a microcrystalline oxide semiconductor, an amorphous oxide semiconductor, polysilicon, or low-temperature polysilicon (low-temperature polycrystalline silicon (LTPS)).

In the present embodiment, a portion of the gate line GL that overlaps the semiconductor layer 61 serves as the gate electrode 64. Titanium (Ti), aluminum (Al), copper (Cu), silver (Ag), molybdenum (Mo), or an alloy of these metals is used as the gate electrode 64 (gate line GL). A channel area is formed at a portion of the semiconductor layer 61 that overlaps the gate electrode 64.

A portion of the signal line SL that overlaps the semiconductor layer 61 serves as the source electrode 62. The drain electrode 63 extends in the second direction Dy so as to intersect the gate line GL in plan view. An end of the drain electrode 63 is provided with a coupling portion 63*a* in a position overlapping the photodiode PD. The width in the first direction Dx of the coupling portion 63*a* is formed to be larger than the width in the first direction Dx of the drain electrode 63.

The coupling portion 63*a* is coupled, through a contact hole CH2, to lead wiring 67*a* drawn out from coupling wiring 67. The coupling wiring 67 is located at a central portion of the photodiode PD in plan view, and is formed to have a polygonal outline shape (substantially octagonal outline shape). The lead wiring 67*a* is coupled to the coupling wiring 67, and extends in an oblique direction toward the transistor Tr.

The lower electrode 35 of the photodiode PD is coupled to the coupling wiring 67 through a contact hole CH1. The contact hole CH1 is located at the central portion of the photodiode PD in the plan view. The detection device 1 includes an overlapping conductive layer 71 and an insulating layer 26 that covers the overlapping conductive layer 71. In plan view, the overlapping conductive layer 71 and a projecting portion 26*a* of the insulating layer 26 overlap the central portion of the photodiode PD and the coupling wiring 67, and also overlap the contact hole CH1 of a planarizing layer 27. That is, the overlapping conductive layer 71 and the projecting portion 26*a* of the insulating layer 26 are located at the central portion of the photodiode PD in plan view. A coupling configuration of the photodiode PD to the coupling wiring 67, and details of the overlapping conductive layer 71 and the projecting portion 26*a* of the insulating layer 26 will be described later with reference to FIGS. 5 and 6.

The external shape of the coupling wiring 67 is not limited to the polygonal shape and may be another shape such as a circular shape or a quadrilateral shape. The lead wiring 67*a* may be drawn in any way as long as being allowed to be coupled to the coupling portion 63*a* of the drain electrode 63. Alternatively, the lead wiring 67*a* may be eliminated, and the coupling wiring 67 may be coupled to the coupling portion 63*a* of the drain electrode 63. In the following description, the coupling wiring 67 and the lead wiring 67*a* may be simply referred to as the coupling wiring 67 when they need not be distinguished from each other.

For example, the arrangement and the shape of the transistors Tr are also merely exemplary and can be changed as appropriate. For example, the semiconductor layer 61 may have a portion that does not overlap the gate line GL in plan view.

Figure 5:
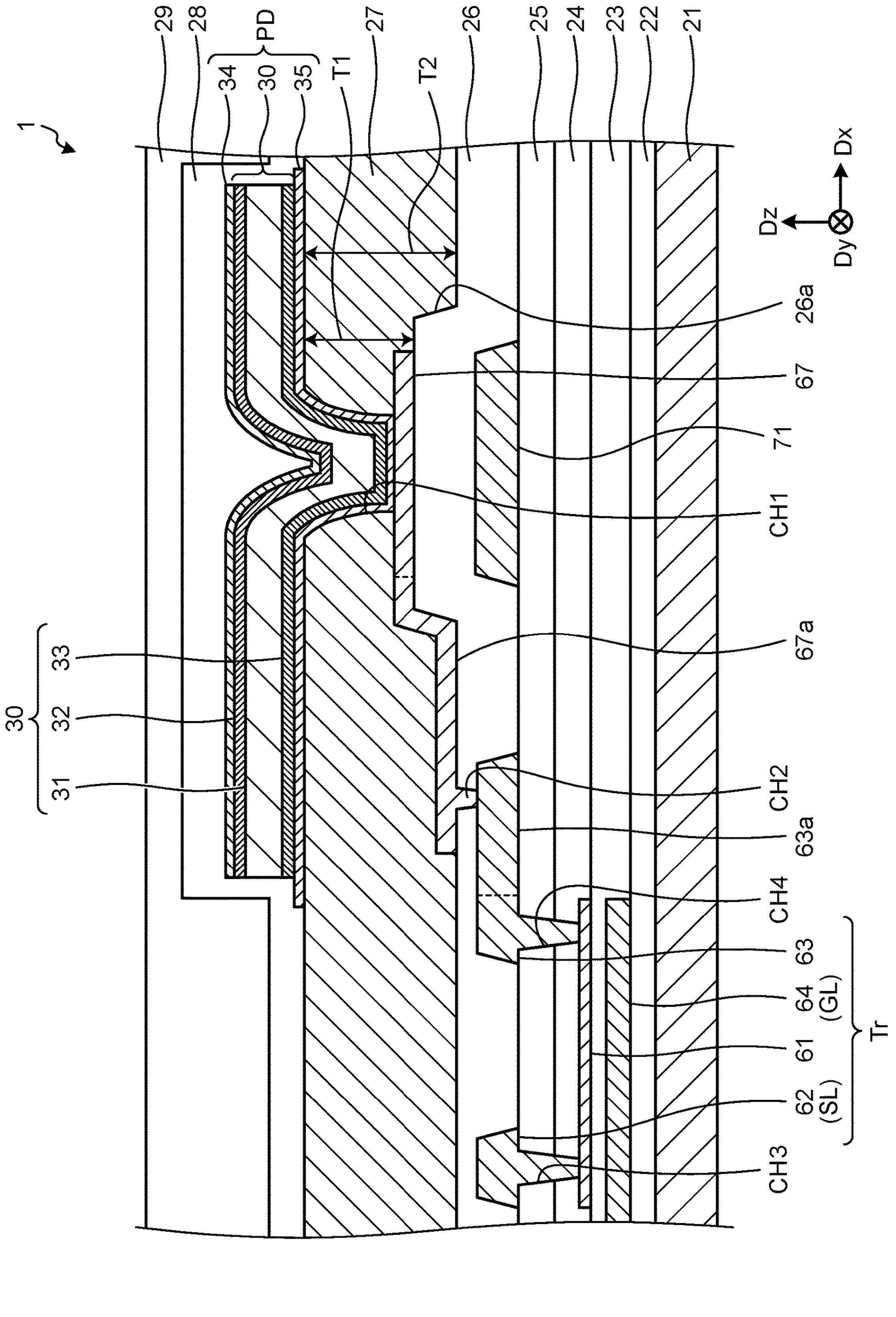
FIG. 5 is a sectional view along V-V' of FIG. 4.

The following describes a multilayered configuration of the detection device 1. FIG. 5 is a sectional view along V-V' of FIG. 4. In the following description, a direction from the substrate 21 toward a sealing film 29 in a direction orthogonal to a surface of the substrate 21 is referred to as "upper side" or simply "above". A direction from the sealing film 29 toward the substrate 21 is referred to as "lower side" or simply "below".

As illustrated in FIG. 5, the substrate 21 is an insulating substrate and is made using, for example, glass or a resin material. The substrate 21 is not limited to having a flat plate shape and may have a curved surface. In this case, the substrate 21 may be a film-like resin substrate.

Insulating layers 22, 23, 24, 25, and 26 are provided on the substrate 21. The insulating layers 22, 23, 24, 25, and 26 are inorganic insulating films of, for example, silicon oxide ($SiO_2$) or silicon nitride (SiN). Each of the inorganic insulating layers is not limited to a single layer and may be a multilayered film.

The gate electrode 64 (gate line GL) is provided on the insulating layer 22. The insulating layer 23 is provided on the insulating layer 22 so as to cover the gate electrode 64 (gate line GL). The semiconductor layer 61 is provided on the insulating layer 23. The insulating layers 24 and 25 are provided on the insulating layer 23 so as to cover the semiconductor layer 61. The insulating layer 22 need not be formed.

The source electrode 62 (signal line SL) and the drain electrode 63 (coupling portion 63*a*) are provided on the insulating layer 25. The source electrode 62 is electrically coupled to the one end side of the semiconductor layer 61 through the contact hole CH3 provided in the insulating layers 24 and 25. The drain electrode 63 is electrically coupled to the other end side of the semiconductor layer 61 through the contact hole CH4 provided in the insulating layers 24 and 25. The drain electrode 63 and the coupling portion 63*a* are provided so as to extend from an area that does not overlap the photodiode PD to an area that overlaps the photodiode PD.

The overlapping conductive layer 71 is provided in the same layer as that of the source electrode 62 (signal line SL) and the drain electrode 63 on the insulating layer 25. In other words, the overlapping conductive layer 71 is provided between the insulating layers 25 and 26. The overlapping conductive layer 71 is formed of the same material as that of the signal line SL and the like. The overlapping conductive layer 71 is formed of, for example, a Mo/Al/Mo (MAM) film that is a multilayered film of molybdenum (Mo) and aluminum (Al). As described above, the overlapping conductive layer 71 is provided in the position overlapping the central portion of the photodiode PD and the coupling wiring 67. The overlapping conductive layer 71 is located between the substrate 21 and a group of the photodiode PD and the coupling wiring 67 in the third direction Dz.

The insulating layer 26 is provided on the insulating layer 25 so as to cover the source electrode 62 (signal line SL), the drain electrode 63 (coupling portion 63*a*), and the overlapping conductive layer 71. In the example illustrated in FIG. 5, at least one of the insulating layers 22, 23, 24, 25, and 26, for example, the insulating layer 26, is provided along a surface of the overlapping conductive layer 71. This configuration raises the insulating layer 26 at a portion thereof overlapping the overlapping conductive layer 71 and forms the projecting portion 26*a* projecting toward the photodiode PD. The thickness of the overlapping conductive layer 71 is approximately 200 nm to 600 nm, for example. The thickness of each of the insulating layers 22, 23, 24, 25, and 26 is approximately 200 nm to 500 nm, for example.

The coupling wiring 67 and the lead wiring 67*a* are provided on the insulating layer 26. The coupling wiring 67 is provided on the projecting portion 26*a* of the insulating layer 26. The lead wiring 67*a* is coupled to the drain electrode 63 (coupling portion 63*a*) through the contact hole CH2 provided in the insulating layer 26. The coupling wiring 67 and the lead wiring 67*a* are provided in the area overlapping the photodiode PD. The thickness of the coupling wiring 67 is 100 nm to 200 nm, for example.

The insulating layer 22 is also called an "undercoat film" and is provided so as to cover the surface of the substrate 21. The insulating layer 23 is also called a "gate insulating film" and insulates the layer of the gate electrode 64 (gate line GL) from the layer of the semiconductor layer 61. The insulating layers 24 and 25 are also called an "interlayer insulating films" and insulate the layer of the semiconductor layer 61 from the layers of the source electrode 62 and the drain electrode 63. The insulating layer 26 is also called a "passivation film" and is provided so as to cover the transistor Tr and the overlapping conductive layer 71.

The planarizing layer 27 is provided on the insulating layer 26 so as to cover the coupling wiring 67 and the lead wiring 67*a*. In other words, the coupling wiring 67 and the lead wiring 67*a* are located between the insulating layer 26 and the planarizing layer 27 in the third direction Dz and electrically coupled to the photodiode PD. The planarizing layer 27 is an organic insulating film and is formed of an acrylic resin, for example. The planarizing layer 27 is a planarizing layer that is provided so as to cover the transistor Tr and the overlapping conductive layer 71 and planarizes asperities formed by the transistor Tr, the overlapping conductive layer 71, and various types of wiring. In more detail, the planarizing layer 27 is provided so as to cover steps formed by, for example, the projecting portion 26*a* of the insulating layer 26 and the coupling wiring 67. The upper surface of the planarizing layer 27 is substantially flatly formed except in an area overlapping the contact hole CH1.

The following describes a multilayered configuration of the photodiode PD. The photodiode PD is stacked in the order of the lower electrode 35, the semiconductor layer 30, and the upper electrode 34 above the substrate 21, more specifically, on top of the planarizing layer 27. The photodiode PD is provided continuously over the top of the planarizing layer 27 and the area overlapping the contact hole CH1. That is, the lower electrode 35, the semiconductor layer 30, and the upper electrode 34 included in the photodiode PD are provided on the planarizing layer 27 and cover the contact hole CH1. The insulating layers 22, 23, 24, 25, 26 and the planarizing layer 27 are provided between the layers of the substrate 21 and the photodiode PD.

The lower electrode 35 is provided on the planarizing layer 27, contacts the coupling wiring 67 at the bottom of the contact hole CH1 provided in the planarizing layer 27, and is electrically coupled to the transistor Tr. The contact hole CH1 provided in the planarizing layer 27 is provided at the central portion of the photodiode PD in plan view (refer to FIG. 4). The lower electrode 35 is the anode of the photodiode PD, and is an electrode for reading the detection signal Vdet. For example, a metal material such as molybdenum (Mo) or aluminum (Al) is used as the lower electrode 35. Alternatively, the lower electrode 35 may be a multilayered film formed by stacking a plurality of layers of these metal materials. The lower electrode 35 may be a light-transmitting conductive material, such as indium tin oxide (ITO) or indium zinc oxide (IZO). The thickness of the lower electrode 35 is approximately 100 nm, for example.

The semiconductor layer 30 includes an i-type semiconductor layer 31, a p-type semiconductor layer 32, and an n-type semiconductor layer 33. The i-type semiconductor layer 31, the p-type semiconductor layer 32, and the n-type semiconductor layer 33 are formed of amorphous silicon (a-Si), for example. In FIG. 5, the n-type semiconductor layer 33, the i-type semiconductor layer 31, and the p-type semiconductor layer 32 are stacked in this order in the direction orthogonal to the surface of the substrate 21. However, the semiconductor layer 30 may have a reversed configuration, that is, the p-type semiconductor layer 32, the i-type semiconductor layer 31, and the n-type semiconductor layer 33 may be stacked in this order. The thickness of the semiconductor layer 30 is approximately 1 μm, for example.

The a-Si of the p-type semiconductor layer 32 is doped with impurities to form a p+ region. The a-Si of the n-type semiconductor layer 33 is doped with impurities to form an n+ region. The i-type semiconductor layer 31 is, for example, a non-doped intrinsic semiconductor, and has lower conductivity than that of the p-type semiconductor layer 32 and the n-type semiconductor layer 33.

The upper electrode 34 is the cathode of the photodiode PD, and is an electrode for supplying the power supply potential SVS to the semiconductor layer 30. The upper electrode 34 is a light-transmitting conductive layer of ITO, for example. A plurality of the upper electrodes 34 are provided in the respective photodiodes PD. The thickness of the upper electrode 34 is approximately 100 nm, for example.

An insulating layer 28 and the sealing film 29 are provided above the planarizing layer 27 so as to cover the photodiode PD. An inorganic insulating film, such as a silicon nitride film or an aluminum oxide film, or a resin film, such as an acrylic film, is used as each of the insulating layer 28 and the sealing film 29. The sealing film 29 is not limited to a single layer and may be a multilayered film having two or more layers obtained by combining the inorganic film with the resin film mentioned above. The sealing film 29 well seals the photodiode PD, and thus can restrain water from entering the photodiode PD from the upper surface side thereof.

Figure 6:
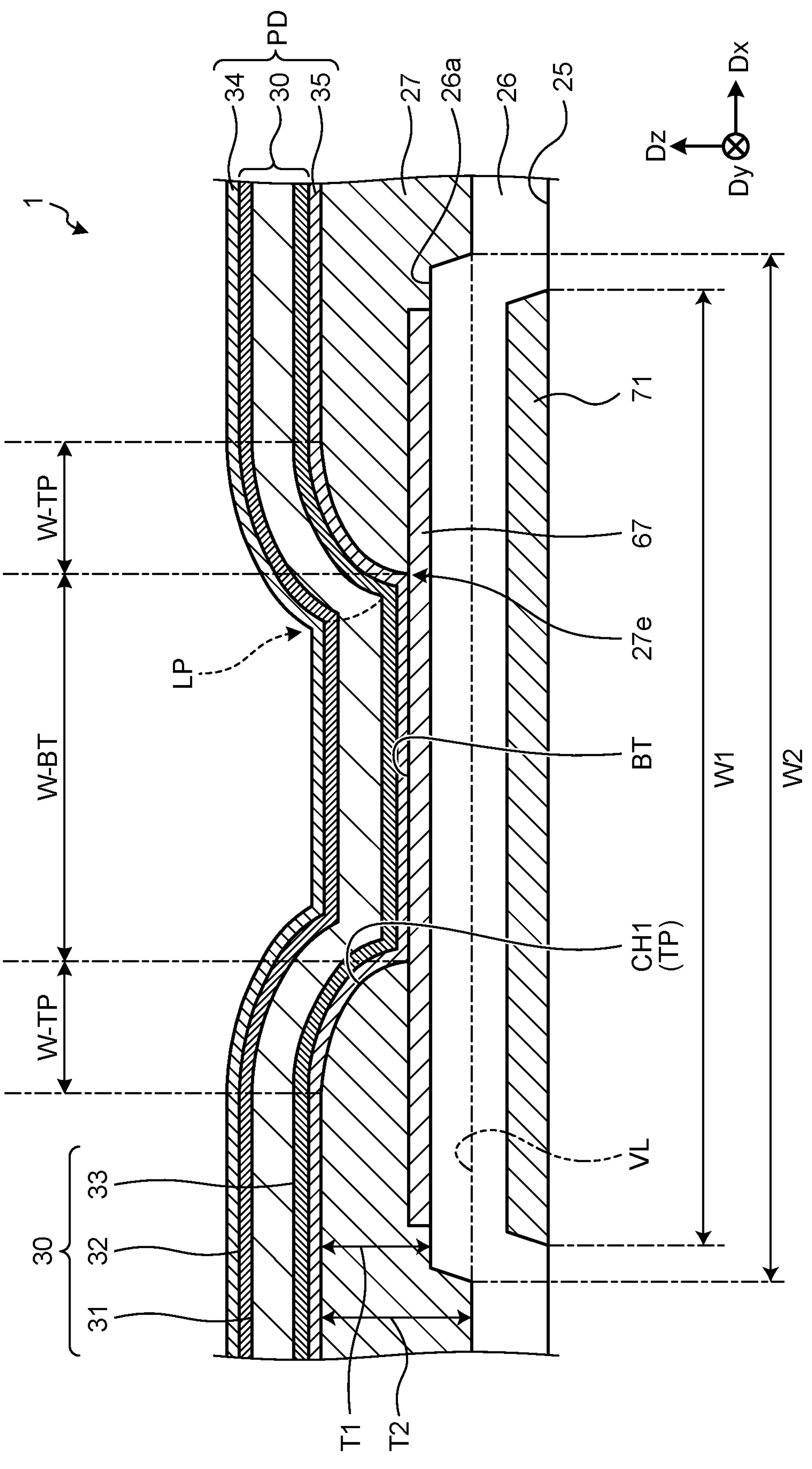
FIG. 6 is a sectional view along VI-VI' of FIG. 4.

The following describes a configuration of the photodiode PD at and near the contact hole CH1, the projecting portion 26*a* of the insulating layer 26, and the overlapping conductive layer 71. FIG. 6 is a sectional view along VI-VI' of FIG. 4. In FIG. 4, in order to illustrate line VI-VI', line VI-VI' is offset from line V-V', but FIGS. 5 and 6 both illustrate the section passing through the center of the contact hole CH1 (centroid of a bottom BT) in plan view.

As illustrated in FIG. 6, the lower electrode 35, the semiconductor layer 30, and the upper electrode 34 of the photodiode PD are provided on the planarizing layer 27 and is also provided continuously in the area overlapping the contact hole CH1. In more detail, the lower electrode 35, the semiconductor layer 30, and the upper electrode 34 are provided continuously across the bottom BT and inclined surfaces TP of the contact hole CH1. The lower electrode 35 is coupled to the coupling wiring 67 at the bottom BT of the contact hole CH1. This configuration electrically couples the photodiode PD to the transistor Tr through the contact hole CH1 and the coupling wiring 67.

A width W-BT in the first direction Dx of the bottom BT of the contact hole CH1 is larger than a width W-TP in the first direction Dx of each of the inclined surfaces TP. In the sectional view, the bottom BT of contact hole CH1 is located between the two inclined surfaces TP. The width W-BT in the first direction Dx of the bottom BT is larger than the width W-TP in the first direction Dx of at least one of the inclined surfaces TP. The width W-BT of the bottom BT is approximately 10 μm, for example, and the width W-TP of the inclined surface TP is approximately 4 μm to 5 μm, for example. The lengths of, for example, the width W-BT and the width W-TP are lengths in the same section cut along an imaginary line that passes through the centroid of the bottom BT of contact hole CH1 in plan view and is parallel to the first direction Dx.

As described above, the overlapping conductive layer 71 is provided between the insulating layers 25 and 26. This configuration causes the insulating layer 26 to have the projecting portion 26*a* projecting toward the photodiode PD in the direction orthogonal to the substrate 21. The overlapping conductive layer 71 and the projecting portion 26*a* of the insulating layer 26 are provided at the central portion of the photodiode PD in plan view. The contact hole CH1 provided in the planarizing layer 27 is provided in a position at the central portion of the photodiode PD in plan view that overlaps the projecting portion 26*a* of the insulating layer 26.

A thickness T1 of the planarizing layer 27 in an area of the insulating layer 26 that is provided with the projecting portion 26*a* and does not overlap the contact hole CH1, is smaller than a thickness T2 of the planarizing layer 27 in an area of the insulating layer 26 not provided with the projecting portion 26*a*. The thickness T1 is the distance between the upper surface of the projecting portion 26*a* and the upper surface of the planarizing layer 27 in the third direction Dz. The thickness T2 is the distance between the upper surface of the insulating layer 26 and the upper surface of the planarizing layer 27 in the third direction Dz. The difference between the thicknesses T1 and T2 of the planarizing layer 27 (the height of the projecting portion 26*a*) is ideally equal to the film thickness of the overlapping conductive layer 71. The thickness T2 of the planarizing layer 27 is approximately 2 μm, for example.

The width W1 in the first direction Dx of the overlapping conductive layer 71 and the width W2 in the first direction Dx of the projecting portion 26*a* of the insulating layer 26 are both larger than the width in the first direction Dx of the contact hole CH1 (sum of the widths W-TP, W-BT, and W-TP). The width W2 of the projecting portion 26*a* of the insulating layer 26 is larger than at least the width W-BT of the bottom BT of the contact hole CH1.

Because of the overlapping conductive layer 71 and the projecting portion 26*a* of the insulating layer 26, the bottom BT of the contact hole CH1 is located above the height position of the upper surface the insulating layer 26 (the upper surface of a portion of the insulating layer 26 not provided with the projecting portion 26*a*). This configuration can make the step formed by the contact hole CH1 of the planarizing layer 27 smaller than in a configuration not provided with the overlapping conductive layer 71 and the projecting portion 26*a* of the insulating layer 26. The "step formed by the contact hole CH1" refers to a distance in the third direction Dz between the upper surface of the planarizing layer 27 at the periphery of the contact hole CH1 and the bottom BT of contact hole CH1 (the coupling wiring 67).

If the projecting portion 26*a* of the insulating layer 26 is not provided and the step formed by the contact hole CH1 of the planarizing layer 27 is larger, a leak path LP such as a seam of the semiconductor layer 30 may be generated, as illustrated in FIG. 6. The leak path LP such as the seam of the semiconductor layer 30 is generated from a starting point where, for example, a lower end 27*e* of the inclined surface TP of the planarizing layer 27 bends and contacts the coupling wiring 67.

In the present embodiment, the configuration described above forms the smaller step of the contact hole CH1, and the photodiode PD (the lower electrode 35, the semiconductor layer 30, and the upper electrode 34) is provided along the step of the contact hole CH1. The photodiode PD in the contact hole CH1 is provided at a smaller inclination angle along the inclined surface TP of the planarizing layer 27. For example, the inclination angle of the inclined surface TP of the contact hole CH1 is preferably gently formed at 30° or smaller. This configuration reduces the generation of the leak path LP such as the seam of the semiconductor layer 30 that would be caused by the step in the contact hole CH1, in the present embodiment. As a result, the detection device 1 can reduce occurrences of short circuits between the upper electrode 34 and the lower electrode 35.

In addition, compared with the configuration not provided with the overlapping conductive layer 71 and the projecting portion 26*a* of the insulating layer 26, the configuration of the present embodiment can reduce the inclination angle of the inclined surface TP of the contact hole CH1 while keeping the width W-TP constant. In other words, the opening width of the contact hole CH1 (sum of the widths W-TP, W-BT, and W-TP) need not be increased to gently form the inclined surface TP of the contact hole CH1. As a result, the area of the contact hole CH1 including the inclined surface TP and the bottom BT can be reduced relative to the area of the entire photodiode PD. As described above, the detection device 1 can improve the detection sensitivity by restraining a reduction in effective light-receiving area of the photodiode PD, and can also reduce the occurrence of a short circuit between the upper electrode 34 and the lower electrode 35.

As illustrated in FIG. 4, the coupling wiring 67 is provided with a coupling portion 67*s*. The coupling portion 67*s* is provided so as to extend in the second direction Dy from the coupling wiring 67 at a location thereof different from that of the lead wiring 67*a*. The overlapping conductive layer 71 is provided with a coupling portion 71*s*. The coupling portion 71*s* extends along the coupling portion 67*s* and is provided so as to overlap the coupling portion 67*s*. The coupling portion 71*s* is electrically coupled to the coupling portion 67*s* through a contact hole CH5.

This configuration electrically couples the overlapping conductive layer 71 to the coupling wiring 67 in the area overlapping the photodiode PD. The overlapping conductive layer 71 is supplied with the same voltage signal as that of the coupling wiring 67 and the lower electrode 35 of the photodiode PD. That is, the overlapping conductive layer 71 has the same potential as that of the coupling wiring 67 and the lower electrode 35 of the photodiode PD. This configuration can reduce the parasitic capacitance between the overlapping conductive layer 71 and the coupling wiring 67. Since the overlapping conductive layer 71 is provided, occurrences of unintended variations in potential of the photodiode PD can be reduced even when variations in potential occur in the transistor Tr or various types of wiring on the substrate 21 side.

The coupling portion between the overlapping conductive layer 71 and the coupling wiring 67 can be provided at any location in the area overlapping the photodiode PD. In FIGS. 5 and 6, the height of the projecting portion 26*a* of the insulating layer 26 and the film thickness of the overlapping conductive layer 71 are illustrated in an exaggerated manner for ease of understanding. The height of the projecting portion 26*a* of the insulating layer 26 and the thicknesses of the insulating layers 22, 23, 24, 25, and 26, the planarizing layer 27, the overlapping conductive layer 71, and the photodiode PD are merely exemplary and are not limited to the values mentioned above.

The shapes and the like of the projecting portion 26*a* of the insulating layer 26 and the overlapping conductive layer 71 are merely exemplary and can be changed as appropriate. In FIG. 4, the projecting portion 26*a* of the insulating layer 26 and the overlapping conductive layer 71 are polygonal in plan view. However, the outline shapes of the projecting portion 26*a* of the insulating layer 26 and the overlapping conductive layer 71 are not limited to the polygonal shapes and may be circular, quadrilateral, or other shapes. The outline shapes of the projecting portion 26*a* of the insulating layer 26 and the overlapping conductive layer 71 may differ from the outline shape of the coupling wiring 67.

First Modification of First Embodiment

Figure 7:
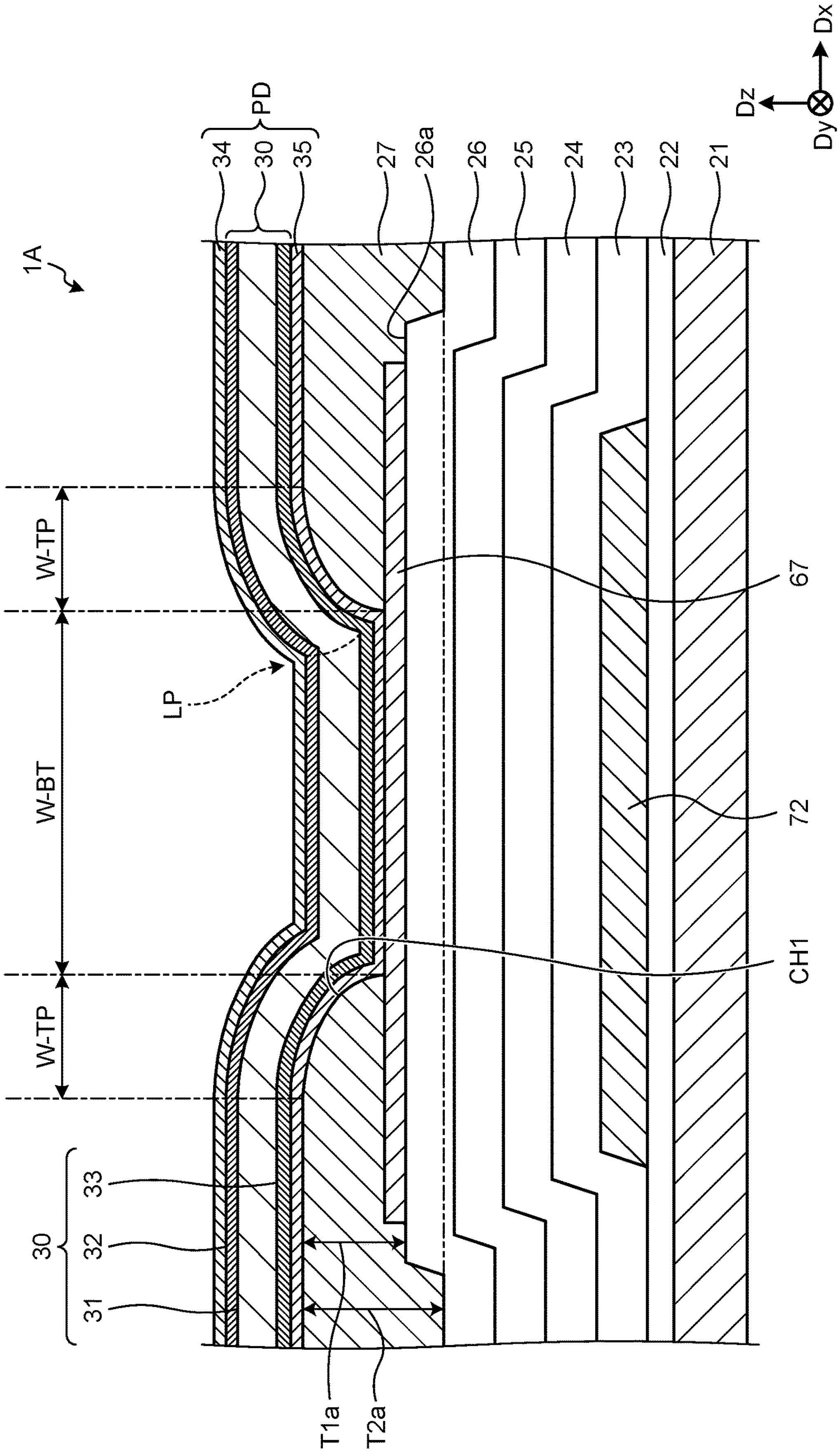
FIG. 7 is a sectional view schematically illustrating a detection device according to a first modification of the first embodiment.

FIG. 7 is a sectional view schematically illustrating a detection device according to a first modification of the first embodiment. In the following description, the same components as those described in the embodiment described above are denoted by the same reference numerals, and the description thereof will not be repeated.

As illustrated in FIG. 7, in a detection device 1A according to the first modification of the first embodiment, an overlapping conductive layer 72 is provided on the insulating layer 22. The overlapping conductive layer 72 is formed in the same layer as that of the gate electrode 64 (gate line GL) (refer to FIG. 5), and of the same material as that of the gate electrode 64 (gate line GL). In other words, the overlapping conductive layer 72 is provided between the insulating layers 22 and 23. The thickness of the overlapping conductive layer 72 is approximately 200 nm to 600 nm, for example.

The insulating layers 23, 24, 25, and 26 are each provided along a surface of the overlapping conductive layer 72. This configuration forms the projecting portion 26*a* projecting toward the photodiode PD at a portion of the topmost insulating layer 26 of the insulating layers 23, 24, 25, and 26 that overlaps the overlapping conductive layer 72.

Also in the present modification, a thickness T1*a* of the planarizing layer 27 in the area of the insulating layer 26 that is provided with the projecting portion 26*a* and does not overlap the contact hole CH1, is smaller than a thickness T2*a* of the planarizing layer 27 in the area of the insulating layer 26 not provided with the projecting portion 26*a*. As a result, the step formed by the contact hole CH1 in the planarizing layer 27 can also be made smaller in the first modification.

The overlapping conductive layer 72 is not limited to being the same layer as that of the gate electrode 64 (gate line GL) (refer to FIG. 5). The overlapping conductive layer 72 may be provided between the insulating layers 23 and 24, or between the insulating layers 24 and 25. The overlapping conductive layer is not limited to one layer of the overlapping conductive layer 72, and a plurality of overlapping conductive layers may be provided in an area overlapping the contact hole CH1 of the planarizing layer 27. For example, the overlapping conductive layer 71 illustrated in the first embodiment may be combined with the overlapping conductive layer 72 illustrated in the first modification.

Second Embodiment

Figure 8:
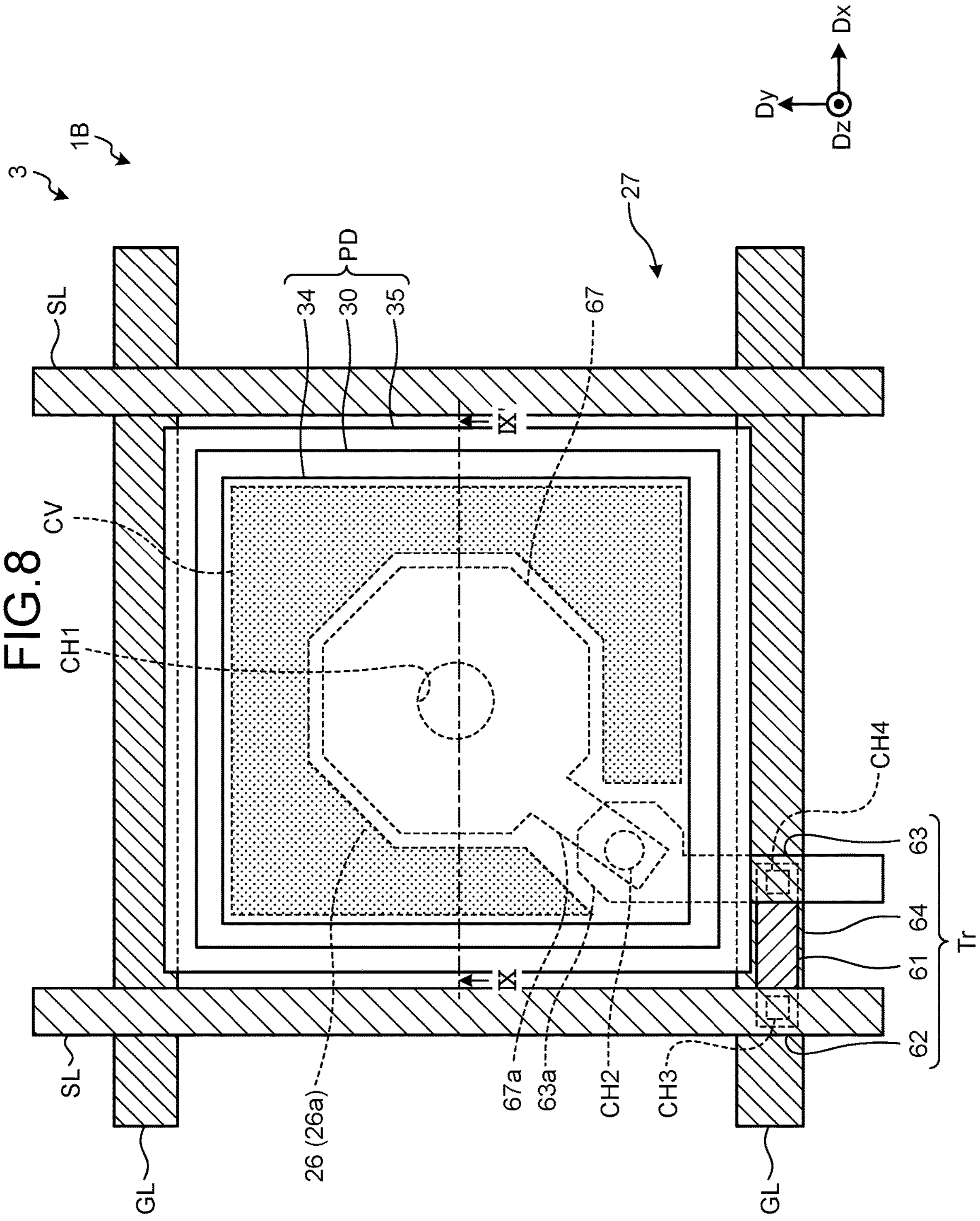
FIG. 8 is a plan view schematically illustrating the photodiode and the transistor of a detection device according to a second embodiment.
Figure 9:
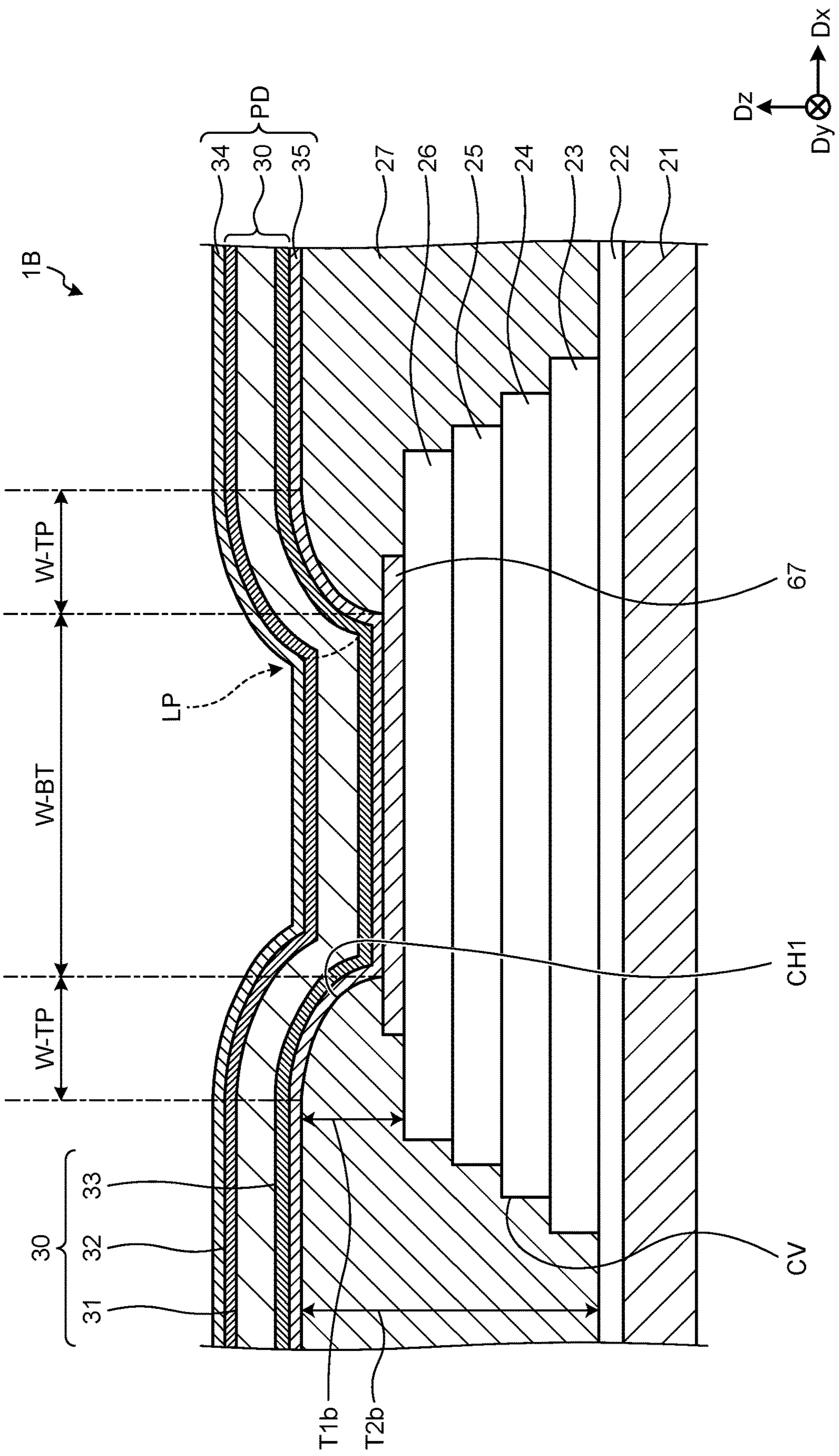
FIG. 9 is a sectional view along IX-IX' of FIG. 8.

FIG. 8 is a plan view schematically illustrating the photodiode and the transistor of a detection device according to a second embodiment. FIG. 9 is a sectional view along IX-IX' of FIG. 8. As illustrated in FIGS. 8 and 9, a detection device 1B according to the second embodiment is not provided with the overlapping conductive layers 71 and 72, unlike in the first embodiment and the first modification described above.

In the detection device 1B according to the second embodiment, the insulating layers 23, 24, 25, and 26 have a recessed portion CV formed in a portion of the area overlapping the photodiode PD. As illustrated in FIG. 8, in plan view, the recessed portion CV is formed in an area that overlaps the photodiode PD and does not overlap the contact hole CH1 and various types of wiring such as the coupling wiring 67, the lead wiring 67*a*, and the drain electrode 63 (coupling portion 63*a*). The recessed portion CV is provided so as to surround the contact hole CH1 and the coupling wiring 67. The projecting portion 26*a* of the insulating layer 26 is formed of a portion of the insulating layer 26 surrounded by the recessed portion CV.

In more detail, as illustrated in FIG. 9, the recessed portion CV is formed so as to penetrate the insulating layers 23, 24, 25, and 26 in the thickness direction thereof. The insulating layer 22 forms the bottom of the recessed portion CV. The projecting portion 26*a* is formed by stacking the insulating layers 23, 24, 25, and 26 in a portion where the recessed portion CV is not formed. In the present embodiment, the projecting portion 26*a* projects in the third direction Dz from the bottom of the recessed portion CV (insulating layer 22) toward the photodiode PD.

The planarizing layer 27 is provided so as to cover the recessed portion CV. With this configuration, a thickness T1*b* of the planarizing layer 27 in the area of the insulating layer 26 that is provided with the projecting portion 26*a* and does not overlap the contact hole CH1, is smaller than a thickness T2*b* of the planarizing layer 27 in the area of the insulating layer 26 not provided with the projecting portion 26*a*, that is, in the recessed portion CV. In the present embodiment, since a portion of the planarizing layer 27 is provided inside the recessed portion CV, the thickness T1*b* of the planarizing layer 27 on the upper side of the insulating layer 26 is formed smaller. As a result, in the detection device 1B according to the second embodiment, the step formed by the contact hole CH1 in the planarizing layer 27 can be reduced.

The recessed portion CV is not limited to the example illustrated in FIG. 9 and only needs to be formed in at least one of the insulating layers 23, 24, 25, and 26 (for example, the insulating layer 26). Alternatively, the recessed portion CV may also be provided in the insulating layer 22.

Third Embodiment

Figure 10:
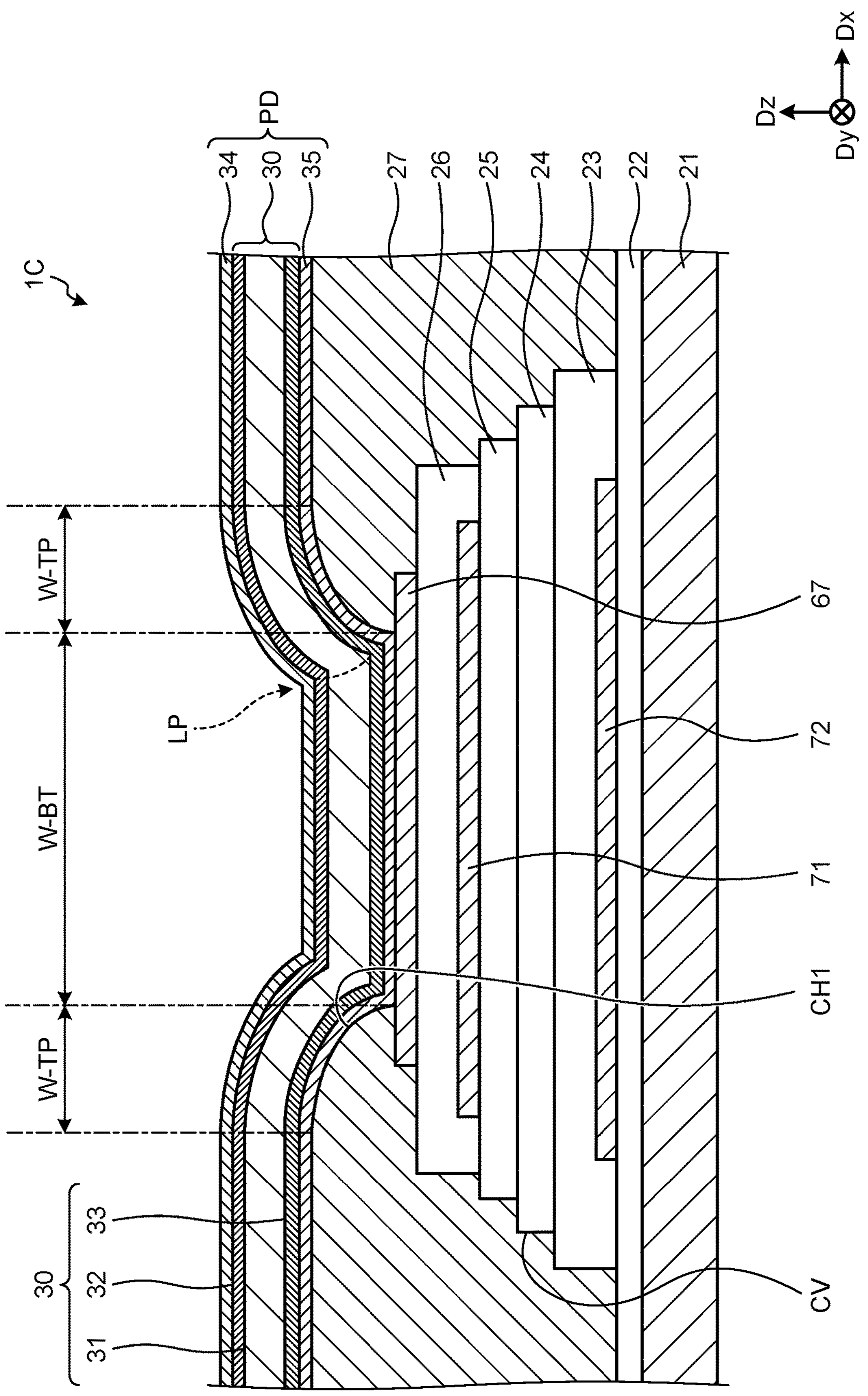
FIG. 10 is a sectional view schematically illustrating a detection device according to a third embodiment.

FIG. 10 is a sectional view schematically illustrating a detection device according to a third embodiment. As illustrated in FIG. 10, a detection device 1C according to the third embodiment has a configuration obtained by combining those of the first embodiment, the second embodiment, and the first modification described above.

That is, the detection device 1C includes the overlapping conductive layers 71 and 72 and also has the recessed portion CV formed in the insulating layers 23, 24, 25, and 26. The overlapping conductive layers 71 and 72 are provided in the area overlapping the contact hole CH1 of the planarizing layer 27 at the central portion of the photodiode PD.

The overlapping conductive layer 72 is provided between the insulating layers 22 and 23. The overlapping conductive layer 72 raises the insulating layer 23, and increases the total thickness including those of the overlapping conductive layer 72 and the insulating layer 23. In the same manner, the overlapping conductive layer 71 is provided between the insulating layers 25 and 26. The overlapping conductive layer 71 raises the insulating layer 26, and increases the total thickness including those of the overlapping conductive layer 71 and the insulating layer 26. As a result, the entire projecting portion 26*a* including the insulating layers 23, 24, 25, and 26 and the overlapping conductive layers 71 and 72 is formed to have a larger height.

In addition, the recessed portion CV is formed so as to penetrate the insulating layers 23, 24, 25, and 26 in the thickness direction thereof. The recessed portion CV is formed in the area that overlaps the photodiode PD and does not overlap the contact hole CH1 and the coupling wiring 67. The planarizing layer 27 is provided so as to cover the recessed portion CV.

In the detection device 1C according to the third embodiment, the step formed by the contact hole CH1 of the planarizing layer 27 can effectively be reduced by integrating the configurations described above.

In FIG. 10, the side surfaces of the insulating layers 23, 24, 25, and 26 that form the inner wall of the recessed portion CV are arranged in a step-like pattern. As a result, the inclination angle of the side surface of the projecting portion 26*a* including the insulating layers 23, 24, 25, and 26 and the overlapping conductive layers 71 and 72 is gently formed.

While the preferred embodiments have been described above, the present disclosure is not limited to the embodiments described above. The content disclosed in the embodiments is merely an example, and can be variously modified within the scope not departing from the gist of the present disclosure. Any modifications appropriately made within the scope not departing from the gist of the present disclosure also naturally belong to the technical scope of the present disclosure. At least one of various omissions, substitutions, and changes of the components can be made without departing from the gist of the embodiments and the modifications described above.

What is claimed is:

1. A detection device comprising:

a substrate;

a photodiode in which a lower electrode, a semiconductor layer, and an upper electrode are stacked on the substrate in the order as listed;

a transistor provided in the photodiode;

an insulating layer provided between the substrate and a layer of the photodiode in a thickness direction orthogonal to the substrate; and a planarizing layer covering the insulating layer, wherein the insulating layer comprises a projecting portion that projects toward the photodiode in the thickness direction orthogonal to the substrate, the planarizing layer has a contact hole provided in a position that is below the photodiode and overlaps the projecting portion of the insulating layer, the photodiode is provided on an upper side of the planarizing layer and is also provided to cover the contact hole, the lower electrode of the photodiode is electrically coupled to the transistor at a bottom of the contact hole, the detection device further comprises:

a plurality of the insulating layers; and an overlapping conductive layer provided between the plurality of the insulating layers and overlapping the contact hole of the planarizing layer in plan view, and the projecting portion is formed at a portion of at least one of the plurality of the insulating layers that overlaps the overlapping conductive layer.

2. The detection device according to claim 1, further comprising a signal line and a gate line each electrically coupled to the transistor, wherein the overlapping conductive layer is provided in the same layer as that of the signal line.

3. The detection device according to claim 1, further comprising a signal line and a gate line each electrically coupled to the transistor, wherein the overlapping conductive layer is provided in the same layer as that of the gate line.

4. The detection device according to claim 1, further comprising coupling wiring provided between the planarizing layer and the plurality of the insulating layers and electrically coupled to the transistor, wherein the overlapping conductive layer is electrically coupled to the coupling wiring in an area overlapping the photodiode.

5. A detection device comprising:

a substrate;

a photodiode in which a lower electrode, a semiconductor layer, and an upper electrode are stacked on the substrate in the order as listed;

a transistor provided in the photodiode;

an insulating layer provided between the substrate and a layer of the photodiode in a thickness direction orthogonal to the substrate; and a planarizing layer covering the insulating layer, wherein the insulating layer comprises a projecting portion that projects toward the photodiode in the thickness direction orthogonal to the substrate, the planarizing layer has a contact hole provided in a position that is below the photodiode and overlaps the projecting portion of the insulating layer, the photodiode is provided on an upper side of the planarizing layer and is also provided to cover the contact hole, the lower electrode of the photodiode is electrically coupled to the transistor at a bottom of the contact hole, the detection device further comprises a recessed portion provided in an area of the insulating layer overlapping the photodiode to surround the contact hole, wherein the projecting portion is formed at a portion of the insulating layer surrounded by the recessed portion, and the planarizing layer is provided to cover the recessed portion.

6. The detection device according to claim 5, comprising a plurality of the insulating layers, wherein the recessed portion is formed to penetrate the plurality of the insulating layers in the thickness direction, and side surfaces of the plurality of the insulating layers that form an inner wall of the recessed portion are provided in a step-like pattern.

7. The detection device according to claim 1, wherein a width of the projecting portion in a first direction parallel to the substrate is larger than a width of the bottom of the contact hole in the first direction.

8. The detection device according to claim 1, wherein a width of the bottom of the contact hole in a first direction parallel to the substrate is larger than a width of an inclined surface of the contact hole in the first direction.

* * * * *